United States Patent [19]

Houbion

[11] 4,129,729

[45] Dec. 12, 1978

[54] 3-PHENACYL AND PHENACYLIDENE PHTHALIMIDINES AND CORRESPONDING NAPHTHOYL DERIVATIVES

[75] Inventor: John A. Houbion, Kirkwood, Mo.

[73] Assignee: Monsanto Company, St. Louis, Mo.

[21] Appl. No.: 867,721

[22] Filed: Jan. 3, 1978

[51] Int. Cl.$^2$ .................. A01N 9/22; C07D 209/46
[52] U.S. Cl. ........................ 542/439; 260/325 PH; 71/96
[58] Field of Search ............... 260/325 PH; 542/438, 542/439

[56] References Cited

U.S. PATENT DOCUMENTS

| | | | |
|---|---|---|---|
| 3,992,189 | 11/1976 | Goddard | 71/96 |
| 3,995,048 | 11/1976 | Nadelson | 260/325 PH |

*Primary Examiner*—Alton D. Rollins
*Attorney, Agent, or Firm*—Arnold H. Cole; Donald W. Peterson

[57] ABSTRACT

Certain 3-phenacyl and phenacylidene phthalimidines, and the corresponding naphthoyl derivatives, are novel compounds which possess biological activity in the treatment of plants to control their growth.

20 Claims, No Drawings

3-PHENACYL AND PHENACYLIDENE PHTHALIMIDINES AND CORRESPONDING NAPHTHOYL DERIVATIVES

This invention relates to novel organic chemical compounds and to their preparation. More particularly, the invention is concerned with certain 3-phenacyl and 3-phenacylidene phthalimidines, and the corresponding naphthoyl derivatives thereof, and to the preparation of such phthalimidines. The compounds of this invention have been found to display biological activity when used in the treatment of plants. Such activity is herbicidal or inhibitory in some cases, while in others, depending upon rate of application, compounds of this invention act to reduce the injury to crop plants which are contacted with other herbicides in the course of destroying indigenously present weeds.

The 3-phenacyl phthalimidines, and their naphthoyl derivatives, of this invention have the formula

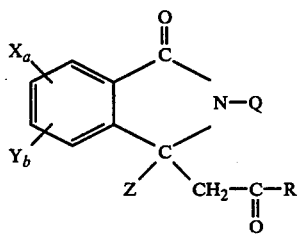

wherein R is phenyl, naphthyl, biphenylyl or substituted phenyl, there being from 1 to 5 substituents selected from alkyl of 1 to 3 carbon atoms, alkoxy of 1 to 4 carbon atoms, halogen, nitro and trifluoromethyl, X is halogen, Y is hydroxy, alkoxy of 1 to 4 carbon atoms, nitro or amino, $a$ is 0 to 4, $b$ is 0 to 2, the sum of $a + b$ is 0 to 4, Z is hydrogen or OH, and Q is hydrogen, alkyl of 1 to 3 carbon atoms, phenyl, halophenyl, nitrophenyl, trifluoromethylphenyl, tolyl, anisyl or tosylamino.

The 3-phenacylidene phthalimidines, and their naphthoyl derivatives, of the invention have the formula

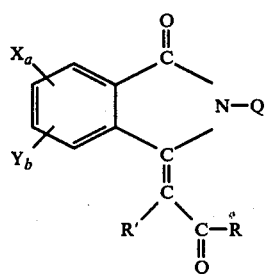

wherein Q, R, X, Y, Z, $a$ and $b$ have the same meaning as above, and R' is hydrogen or bromine.

A variety of 3-substituted phthalimidines are known to the art, and such compounds are also generally substituted in the 2-position. Herbicidal use for 3-methylene phthalimidines is shown in U.S. Pat. No. 3,992,189, while other uses are shown in U.S. Pat. Nos. 3,390,149 and 3,660,428. Herbicidal use is also shown for 3-hydroxy phthalimidines in U.S. Pat. No. 2,857,396, and other uses are shown in U.S. Pat. No. 3,849,938.

The 3-substituted phthalimidines of formula (I) wherein Z is OH can be prepared by reacting, under nondehydrating conditions, equivalent amounts of a 3-substituted phthalide of the formula

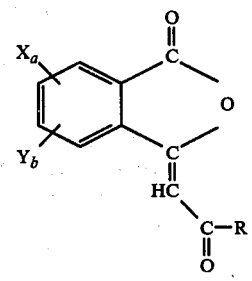

wherein R, X, Y, $a$ and $b$ have the same meanings as above, and ammonia, or a primary aliphatic or aromatic amine. The reaction is preferably carried out in the presence of an inert organic solvent for the phthalide such as tetrahydrofuran, diethyl ether, diisopropyl ether, methyl n-butyl ether and the like. The solvent should have a boiling point below about 100° C. to permit ready separation from the reaction product by distillation at moderate temperatures. This serves to minimize dehydration of the 3-hydroxy group on the phthalimidine product. The primary amines employed in the reaction are those of the formula $H_2N$—Q where Q has the same meaning as above. When the reaction is conducted at temperatures above about 100° C., dehydration takes place to produce a 3-substituted phthalimidine of formula (II).

The 3-substituted phthalimidines of formula I wherein Z is hydrogen can be prepared by a two-step method. In the first step, equivalent amounts of thionyl chloride and a 3-substituted phthalide of the formula

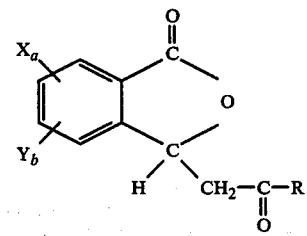

wherein R, X, Y, $a$ and $b$ have the same meanings as above, are reacted together to produce an o-(aroylvinyl)benzoyl chloride. The reaction is preferably carried out in the presence of an inert organic solvent such as benzene, an ether or a chlorinated aliphatic hydrocarbon, and the reactants are heated at reflux temperature. In the second step, the benzoyl chloride is reacted with an equivalent amount of a primary amine, $H_2N$—Q where Q has the same meaning as above. A second equivalent of the same primary amine can be added to serve as an acceptor for hydrogen chloride, and this will help to increase product yield. As an alternative to said second equivalent, a tertiary amine such as triethylamine or pyridine can be employed as the acceptor. This reaction is also preferably carried out in an inert organic solvent such as previously described. External heating is not generally required for this step since the reaction itself is exothermic.

As noted above, the 3-substituted phthalimidines of formula (II) wherein R' is hydrogen can be prepared by dehydration of a corresponding 3-hydroxy phthalimidine of formula (I). The dehydration is conveniently conducted by dissolving the 3-hydroxy compound in an inert organic solvent such as ethanol, preferably containing a small amount of an acidic dehydration catalyst such as hydroboric, hydrochloric, sulfuric or p-toluenesulfonic acid. This solution is heated at reflux temperature for up to several hours to produce the desired product.

To obtain the compounds of formula (II) wherein R' is bromine, a 3-hydroxy phthalimidine of formula (I) is dissolved in a solvent such as glacial acetic acid. One equivalent of molecular bromine dissolved in acetic acid is added slowly at ambient temperature, and the desired brominated product will usually precipitate from the reaction mixture.

The compounds of formula (II) wherein R' is hydrogen can also be prepared in a two-step method. First, a 3-halophthalimidine to the formula

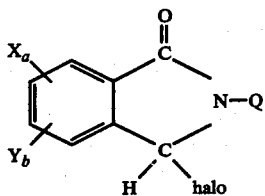

wherein X, Y, Q, a and b have the same meaning as above, is reacted with an equivalent amount of a trialkyl phosphite, P(O Alkyl)$_3$, to give a phosphonate of the formula

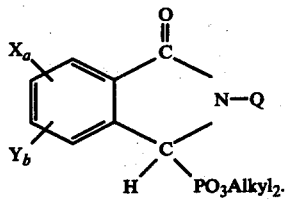

This phosphonate is in turn reacted with an aromatic glyoxal wherein the aromatic group is the same as R. The glyoxal is dissolved in an inert organic solvent such as methanol, and said solvent should contain an amount of sodium methoxide sufficient to displace the phosphonate group. This reaction usually proceeds at room temperature, but gentle heating can be employed if desired to accelerate precipitation of the phthalimidine product of formula (II).

In an alternative procedure, a 3-halophthalimidine is first reacted with a trialkyl phosphine, P Alkyl$_3$, to product a phosphonium salt of the formula

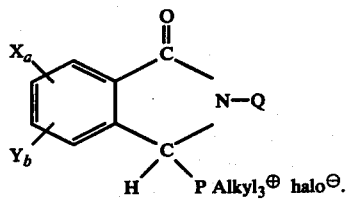

Said salt is then reacted with an aromatic glyoxal, as described above, in the presence of an organic base. The product is a 3-substituted phthalimidine of formula (II) wherein R' is hydrogen. The 3-halophthalimidines employed as starting materials are obtained by first reacting a 3-hydroxyphthalide with an aromatic amine such as aniline. The reaction product is then reacted with a thionyl halide to produce said 3-halo compound. Chlorine is the preferred halogen.

It will be recognized that the phthalimidines of formula (I) of this invention contain an asymmetric carbon atom and hence may exist in two stereoisomeric forms. Both stereoisomeric forms, together with mixtures thereof, fall within the scope of the invention. It will further be recognized that the phthalimidines of formula (II) of this invention contain a carbon-to-carbon double bond with two different groups or atoms attached to each carbon. Such compounds may thus exist in the form of cis and trans geometric isomers, and both of said isomers, along with mixtures thereof, are contemplated within the scope of this invention.

The following illustrative, non-limiting examples will serve to further demonstrate to those skilled in the art the manner in which specific compounds within the scope of the invention can be prepared. It should be understood that while equivalent or stoichiometric amounts of reactants are generally employed, a molar excess of reactants can be substituted.

EXAMPLE 1

A suspension of 15.7 grams (52.5 mmol) of 3-(α-naphthoylmethylene)phthalide in 200 ml of methylene chloride and 100 ml of tetrahydrofuran was stirred at room temperature. Dry ammonia was passed through the solution until it became clear. After 1 hour, the solvents were evaporated under vacuum, and the residue was recrystallized from ethanol/water to yield 11 grams of 3-hydroxy-3-(α-naphthoylmethyl)phthalimidine, m.p. 148°–150° C. Analysis shows 75.62% carbon, 4.82% hydrogen and 4.37% nitrogen as against calculated values of 75.70%, 4.76% and 4.41% for $C_{20}H_{15}NO_3$.

EXAMPLE 2

Into a 100 ml flask provided with a magnetic stirrer and a dry-ice condenser, there was placed 5.5 grams (22 mmol) of 3-phenacylidenephthalide and 50 ml of tetrahydrofuran. Dry ammonia was introduced over a 15 minute period, and the solution was allowed to come to room temperature upon which the excess ammonia evaporated. The solution was then concentrated, and the residue was recrystallized from tetrahydrofuran/ligroin to yield 5.5 grams of 3-hydroxy-3-phenacyl phthalimidine, m.p. 128°–129° C. Analysis shows 67.42% carbon, 5.30% hydrogen and 4.90% nitrogen as against calculated values of 67.36%, 5.30% and 4.91% for $C_{16}H_{13}NO_3$.

By substituting 4,5,6,7-tetrachloro-3-phenacylidenephthalide as the initial reactant in the above example, the product obtained is 4,5,6,7-tetrachloro-3-hydroxy-3-phenacyl phthalimidine. Similarly, when the initial reactant is 6-nitro-3-phenacylidenephthalide, the product obtained is 6-nitro-3-hydroxy-3-phenacyl phthalimidine.

EXAMPLE 3

An excess of ammonia was added dropwise by means of a dry-ice condenser to a solution of 2.4 grams (9 mmol) of 3-(4'-fluorophenacylidene)phthalide and 50 ml of tetrahydrofuran. The solution was allowed to warm to room temperature and concentrated. The solid residue was recrystallized from n-hexane/acetone to yield 1.7 grams of 3-hydroxy-3-(4'-fluorophenacyl) phthalimidine, m.p. 141° C. Analysis shows 67.40% carbon, 4.24% hydrogen and 4.95% nitrogen as against calculated values of 67.36%, 4.24% and 4.91% for $C_{16}H_{21}FNO_3$.

EXAMPLE 4

A 5.6 grams (19 mmol) portion of 3-(4'-chlorophenacylidene)phthalide in 80 ml of anhydrous tetrahydrofuran was stirred and cooled in an ice water bath. Ammonia gas was added by condensation from a dry-ice-acetone condenser. Ammonia was allowed to drip into the reaction mixture for about 20 minutes. The mixture was stirred until the dry-ice completely evaporated, and it was then heated at 30° C. for 20 minutes to remove excess ammonia. The solvent was stripped to give a yellow oil which crystallized on standing to a yellowish white solid. Recrystallization from methylene chloride yielded 3.5 grams of 3-hydroxy-3-(4'-chlorophenacyl)phthalimidine, m.p. 147°–148° C. Analysis shows 63.63% carbon, 4.05% hydrogen, 11.80% chlorine and 4.64% nitrogen as against calculated values of 63.69%, 4.01%, 11.75% and 4.64% for $C_{16}H_{12}ClNO_3$.

By substituting 3-(2',3',5',6'-tetrafluoro-4'-methoxyphenacylidene)phthalide as the initial reactant in the above example, the product obtained is 3-hydroxy-3-(2',3',5',6'-tetrafluoro-4'-methoxyphenacyl)phthalimidine. Similarly, when the initial reaction is 6-methoxy-3-phenacylidenephthalide, the product obtained is 6-methoxy-3-hydroxy-3-phenacyl phthalimidine.

EXAMPLE 5

Following the procedures described in Example 4, 3-(4'-bromophenacylidene)phthalide was employed as the starting material. The product obtained was 3-hydroxy-3-(4'-bromophenacyl)phthalimidine, m.p. 158°–159° C. Analysis shows 55.75% carbon and 3.45% hydrogen as against calculated values of 55.51% and 3.49% for $C_{16}H_{12}BrNO_3$.

EXAMPLE 6

Following the procedures described in Example 4, 3-(4'-phenylphenacylidene)phthalide was employed as the starting material. The product obtained was 3-hydroxy-3-(4'-phenylphenacyl)phthalimidine, m.p. 175°–176° C. Analysis shows 76.93% carbon, 5.00% hydrogen and 4.07% nitrogen as against calculated values of 76.95%, 4.99% and 4.08% for $C_{22}H_{17}NO_3$.

EXAMPLE 7

Following the procedures described in Example 4, 3-(3',4'-dimethoxyphenacylidene)phthalide was employed as the starting material. The product obtained was 3-hydroxy-3-(3',4'-dimethoxyphenacyl)phthalimidine, m.p. 161°–162° C. Analysis shows 66.12% carbon, 5.23% hydrogen and 4.29% oxygen as against calculated values of 66.05%, 5.23% and 4.28% for $C_{18}H_{17}NO_5$.

EXAMPLE 8

A 2.5 grams (10 mmol) portion of 3-phenacylidenephthalide was stirred and heated to 60° C. in a pressure bottle with 0.67 gram (10 mmol) of methylamine hydrochloride and 1.2 grams (12 mmol) of triethylamine in 50 ml of tetrahydrofuran for 10 hours. Water was added, and the product was extracted with methylene chloride. The solvent was stripped to give a yellow oil, and the oil was triturated with anhydrous diethyl ether which precipitated a white solid. Upon filtration there was obtained 0.4 gram of 2-methyl-3-hydroxy-3-phenacyl phthalimidine as a white solid, m.p. 108°–109° C. Analysis shows 72.60% carbon, 5.40% hydrogen and 4.91% nitrogen as against calculated values of 72.58%, 5.37% and 4.98% for $C_{17}H_{15}NO_3$.

EXAMPLE 9

Following the procedures described in Example 4, 3-(2'-chlorophenacylidene)phthalide was employed as the starting material. The product obtained was 3-hydroxy-3-(2'-chlorophenacyl)phthalimidine, m.p. 139°–140° C. Analysis shows 63.58% carbon, 4.03% hydrogen, 11.74% chlorine and 4.65% nitrogen as against calculated values of 63.69%, 4.01%, 11.75% and 4.64% for $C_{16}H_{12}ClNO_3$.

EXAMPLE 10

To 7.65 grams (24.4 mmol) of o-(2',4',6'-trimethylbenzoylvinyl)benzoyl chloride dissolved in 35 ml of benzene was added 3.0 grams (24.4 mmol) of p-anisidine. This was followed by the dropwise addition of 2.48 grams (24.4 mmol) of triethylamine in 25 ml of benzene. The reaction became exothermic and was stirred overnight. A salt precipitated and was filtered off, after which 100 ml of benzene was added. The organic layer was washed twice with 50 ml of 1N HCl, then with 50 ml of water and finally concentrated under vacuum. Recrystallization from 160 ml of ethanol-acetone-water (3:1:1) gave 6.4 grams of 2-(p-anisyl)-3-(2',4',6'-trimethylphenacyl)phthalimidine, m.p. 188°–189° C. Analysis shows 78.13% carbon, 6.33% hydrogen and 3.55% nitrogen as against calculated values of 78.17%, 6.31% and 3.51% for $C_{26}H_{35}NO_3$.

EXAMPLE 11

A solution of 27.7 grams (100 mmol) of 3-hydroxy-3-phenacyl phthalimidine in 270 ml of ethanol and 0.1 gram of p-toluenesulfonic acid was heated at reflux for 1 hour. Addition of n-hexane precipitated 24.9 grams of 3-phenacylidene phthalimidine, m.p. 159°–160° C. Analysis gives 77.02% carbon, 4.46% hydrogen and 5.63% nitrogen as against calculated values of 77.10%, 4.45% and 5.62% for $C_{15}H_{11}NO_2$.

EXAMPLE 12

A solution of 5.0 grams (16.7 mmol) of 3-hydroxy-3-(α-naphthoylmethyl)phthalimidine in 20 ml of ethanol was heated at reflux for 2 hours with a trace amount of p-toluenesulfonic acid. Addition of n-hexane precipitated 4.5 grams of 3-(α-naphthoylmethylene)phthalimidine as a yellow solid, m.p. 185°–188° C. Analysis gives 80.16% carbon, 4.40% hydrogen and 4.63% nitrogen as against calculated values of 80.25%, 4.38% and 4.68% for $C_{20}H_{13}NO_2$.

EXAMPLE 13

A 5.3 gram (19 mmol) portion of 3-(2'-methoxyphenacylidene)phthalide was stirred at −32° C. for several hours in 75 ml of tetrahydrofuran and 30 ml of ammonia. The solvent was stripped to give 3-hydroxy-3-(2'-methoxyphenacyl)phthalimidine as a white solid. This product was heated at reflux for several hours in ethanol with a trace of p-toluenesulfonic acid. The solvent was stripped to give a yellow solid which was taken up in methylene chloride, washed with dilute $NaHCO_3$ solution and dried. The solvent was stripped to yield 2.2 grams of 3-(2'-methoxyphenacylidene)phthalimidine as a yellow solid, m.p. 130° C. Analysis gives 72.94% carbon, 4.71% hydrogen and 5.01% nitrogen as against calculated values of 73.11%, 4.69% and 5.02% for $C_{17}H_{13}NO_3$.

EXAMPLE 14

Following the procedures described in Example 13, 3-(3'-methylphenacylidene)phthalide was employed as the starting material. The final product obtained was 3-(3'-methylphenacylidene)phthalimidine, m.p. 134° C. Analysis gives 77.43% carbon, 4.99% hydrogen and 5.39% nitrogen as against calculated values of 77.55%, 4.98% and 5.32% for $C_{17}H_{13}NO_2$.

EXAMPLE 15

A 1.3 gram (4 mmol) portion of 3-hydroxy-3-(2'-chlorophenacyl)phthalimidine was heated at reflux for 2 hours in 35 ml of ethanol with a trace of p-toluenesulfonic acid. The solvent was stripped, and the solid was taken up in methylene chloride. It was then washed with dilute aqueous $NaHCO_3$ solution, dried and stripped to give a yellow solid. Recrystallization from methylene chloride and carbon tetrachloride yielded 0.9 grams of 3-(2'-chlorophenacylidene)phthalimidine as a yellow solid, m.p. 153° C. Analysis gives 67.58% carbon, 3.61% hydrogen, 12.65% chlorine and 4.84% nitrogen as against calculated values of 67.74%, 3.55%, 12.50% and 4.94% for $C_{16}H_{10}ClNO_2$.

EXAMPLE 16

Following the procedures described in Example 15, 3-hydroxy-3-(3',4'-dimethoxyphenacyl)phthalimidine was employed as the starting material. The product obtained was 3-(3',4'-dimethoxyphenacylidene)phthalimidine, m.p. 198°–199° C. Analysis gives 69.81% carbon, 4.88% hydrogen and 4.61% nitrogen as against calculated values of 69.89%, 4.89% and 4.53% for $C_{18}H_{15}NO_4$.

EXAMPLE 17

Following the procedures described in Example 15, 3-hydroxy-3-(4'-bromophenacyl)phthalimidine was employed as the starting material. The product obtained was 3-(4'-bromophenacylidene)phthalimidine, m.p. 250° C. Analysis gives 58.61% carbon, 3.07% hydrogen, 24.26% bromine and 4.31% nitrogen as against calculated values of 58.60%, 3.05%, 24.38% and 4.27% for $C_{16}H_{10}BrNO_2$.

EXAMPLE 18

A suspension of 10.5 grams (32.5 mmol) of 3-(4'-butoxyphenacylidene)phthalide in 100 ml of dry tetrahydrofuran was saturated with ammonia. After stirring for 30 minutes at 25° C., the solvent was evaporated, 100 ml of benzene was added, and the solution was heated at reflux for 30 minutes in the presence of crystals of p-toluenesulfonic acid. Hot water washing and recrystallization from benzene/heptane gave 9.5 grams of 3-(4'-butoxyphenacylidene)phthalimidine, m.p. 147° C. Analysis shows 74.71% carbon, 5.96% hydrogen and 4.32% nitrogen as against calculated values of 74.75%, 5.96% and 4.36% for $C_{20}H_{19}NO_3$.

EXAMPLE 19

A solution of 2.5 grams (10 mmol) of 3-phenacylidene phthalide, 1.3 grams (11 mmol) of p-anisidine and 20 ml of o-dichlorobenzene was heated at reflux for 3 hours. After cooling, about 0.3 grams of yellow precipitate consisting of unreacted starting material was filtered off. Ligroin was added to the filtrate to precipitate 2.5 grams of 2-(p-methoxyphenyl)-3-phenacylidene phthalimidine, m.p. 153°. Analysis shows 76.93% carbon, 4.65% hydrogen and 4.06% nitrogen as against calculated values of 77.33%, 4.82% and 3.94% for $C_{23}H_{17}NO_3$.

EXAMPLE 20

A solution of 5.4 grams (34 mmol) of bromine in 20 ml of acetic acid was added dropwise, with stirring at 35° C., to 8.2 grams (31 mmol) of 3-hydroxy-3-phenacyl phthalimidine in 100 ml of glacial acetic acid. A fine precipitate appeared, and the slurry was slowly poured into ice cold water. A yellowish solid was separated, dissolved in methylene chloride and washed twice with water until neutral to litmus. Recrystallization from ethanol gave 5.0 grams of 3-(α-bromophenacylidene)phthalimidine, m.p. 207°–208° C. Analysis shows 58.40% carbon, 3.05% hydrogen, 4.28% nitrogen and 24.46% bromine as against calculated values of 58.56%, 3.07% and 4.27% and 24.35% for $C_{16}H_{10}BrNO_2$.

EXAMPLE 21

To 18.1 grams (50 mmol) of 2-(4'-nitrophenyl)-3-diethylphosphonyl phthalimidine and 6.7 grams (50 mmol) of phenylglyoxal in 100 ml of methanol, there was slowly added 10.8 grams of 25% sodium methoxide in methanol with vigorous stirring. The precipitate was filtered off and washed with small amounts of methanol. Recrystallization from ethanol and pyridine gave 15.5 grams of 2-(p-nitrophenyl)-3-phenacylidene phthalimidine as yellow crystals, m.p. 195°–196° C. Analysis shows 71.37% carbon, 3.85% hydrogen and 7.62% nitrogen as against calculated values of 71.35%, 3.81% and 7.56% for $C_{22}H_{14}N_2O_4$.

EXAMPLE 22

A mixture of 4.6 grams (14.6 mmol) of 2-(3'-trifluoromethylphenyl)-3-dimethylphosphonyl phthalimidine prepared by reacting trimethyl phosphite with 2-(3'-trifluoromethylphenyl)-3-chlorophthalimidine and 2.28 grams (15 mmol) of phenylglyoxal was stirred at room temperature in 40 ml of anhydrous methanol. A 3.25 gram (15 mmol) portion of 25% sodium methoxide in 10 ml of methanol was added dropwise, followed by an additional 25 ml of methanol. After stirring the slurry with gentle heating for 30 minutes, the yellow solid was filtered off and washed with cold methanol. Drying under an infrared heating unit yielded 3.7 grams of 2-(3'-trifluoromethylphenyl)-3-phenacylidene phthalimidine, m.p. 174° C. Analysis shows 70.41% carbon, 3.56% hydrogen and 3.62% nitrogen as against calculated values of 70.23%, 3.59% and 3.56% for $C_{23}H_{14}F_3NO_2$.

EXAMPLE 23

A 3.5 gram (13 mmol) portion of 3-hydroxy-3-(4'-chlorophenacyl)phthalimidine was dissolved in ethanol with a trace of p-toluenesulfonic acid. The reaction mixture was heated at reflux for 24 hours, and a yellow precipitate formed. The solid was filtered and dissolved in methylene chloride. The solution was washed with dilute $NaHCO_3$, dried over magnesium sulfate and stripped to yield 2.7 grams of 3-(4'-chlorophenacylidene)phthalimidine, m.p. 248°–249° C. Analysis shows 67.71% carbon, 3.55% hydrogen, 12.48% chlorine and 4.94% nitrogen as against calculated values of 67.74%, 3.55%, 12.50% and 4.94% for $C_{16}H_{10}ClNO_2$.

EXAMPLE 24

A 10.8 grams (20 mmol) portion of 2-(4'-tolylamino)-3-tributylphosphonium phthalimidine chloride and 3.05 grams (20 mmol) of phenylglyoxal were stirred at 20° C. in 100 ml of methylene chloride. There was added dropwise 11 grams (50 mmol) of 25% sodium methoxide in methanol, and the mixture was heated at reflux for 1 hour and acidified with concentrated HCl. The organic layer was washed twice with water, dried over magnesium sulfate and evaporated. The yellow solid was recrystallized from ethanol/chloroform to yield 4 grams of 2-(4'-tosylamino)-3-phenacylidene phthalimidine, m.p. 201° C. Analysis gives 66.04% carbon, 4.42% hydrogen and 6.61% nitrogen as against calculated values of 66.01%, 4.34% and 6.69% for $C_{23}H_{18}N_2O_4S$.

EXAMPLE 25

Following the procedures described in Example 24, p-nitrophenylglyoxal was employed as the starting material. The product obtained was 2-(4'-tosylamino)-3-(p-nitrophenacylidene) phthalimidine, m.p. 222°–224° C. Analysis shows 58.99% carbon and 3.60% hydrogen as against calculated values of 59.61% and 3.70% for $C_{23}H_{17}N_3O_6S$.

EXAMPLE 26

A slurry of 6.5 grams (22.8 mmol) of 4-chloro-3-phenacylidene phthalide in 120 ml of tetrahydrofuran was saturated with ammonia with stirring at room temperature. After the solution became clear, the solvent was evaporated, and the residue was heated at reflux in 60 ml of toluene with a trace of p-toluenesulfonic acid for 40 minutes. The organic layer was washed with 50 ml of water, and n-heptane was added to precipitate 6.1 grams of 4-chloro-3-phenacylidene phthalimidine, m.p. 158°–519° C. Analysis shows 67.50% carbon, 3.57% hydrogen, 4.90% nitrogen and 12.61% chlorine as against calculated values of 67.74%, 3.55%, 4.94% and 12.50% for $C_{16}H_{10}ClNO_2$.

EXAMPLE 27

A solution of 2.5 grams (8 mmol) of 5-chloro-3-phenacylidenephthalide in 25 ml of anhydrous tetrahydrofuran was stirred in an ice-water bath. Ammonia gas was added for about 10 minutes by condensation from a dry-ice-acetone condenser. The reaction was allowed to warm to room temperature, and the solvent was stripped to give a yellow solid which was heated at reflux in ethanol with a trace of p-toluenesulfonic acid. The solution turned bright yellow, and a yellow solid precipitated. Recrystallization from methylene chloride and pentane gave 1.1 grams of 5-chloro-3-phenacylidene phthalimidine, m.p. 228° C. Analysis shows 67.73% carbon, 3.56% hydrogen and 4.91% nitrogen as against calculated values of 67.74%, 3.55% and 4.94% for $C_{16}H_{10}ClNO_2$.

By substituting 5,6-dibromo-3-phenacylidenephthalide as the initial reactant in the above example, the product obtained is 5,6-dibromo-3-phenacylidene phthalimidine. Similarly, when the initial reactant is 6-hydroxy-3-phenacylidenephthalide, the product obtained is 6-hydroxy-3-phenacylidene phthalimidine.

EXAMPLE 28

A mixture of 6.6 grams (26.4 mmol) of 3-phenacylidenephthalide and 1.8 grams (26.4 mmol) of methylamine hydrochloride in 50 ml of tetrahydrofuran was cooled to 0° C. in a pressure bottle equipped with a magnetic stirrer. A 2.7 grams (26.5 mmol) portion of triethylamine was added, and the reaction mixture was heated at 30 C. for 1-2 hours. The solution was then concentrated, 50 ml of methylene chloride was added, and the organic layer containing 2-methyl-3-phenacyl phthalimidine was washed with dilute HCl. Refluxing in ethanol in the presence of a trace amount of p-toluenesulfonic acid gave a solid which, upon three recrystallizations from n-hexane yielded 0.5 gram of 2-methyl-3-phenacylidene phthalimidine as yellow crystals, m.p. 85°–86° C. Analysis shows 77.48% carbon, 5.01% hydrogen and 5.27% nitrogen as against calculated values of 77.55%, 4.98% and 5.32% for $C_{17}H_{13}NO_2$.

EXAMPLE 29

A solution of 4.1 grams (13 mmol) of 3-(3',5'-dimethoxyphenacylidene)phthalide in 40 ml of tetrahydrofuran was stirred and cooled in an ice bath. Ammonia gas was added by condensation from a dry-ice-acetone condenser for about 5 minutes, and the solution was stirred until the dry-ice had evaporated. The solvent was stripped yielding a colorless oil that solidified on standing. The solid was dissolved in chloroform, and 3 drops of trifluoroacetic acid was added. The solution turned bright yellow, and the chloroform was condensed on a steam bath and cooled. A yellow solid was precipitated by addition of 3 drops of dimethylsulfoxide. Recrystallization from methylene chloride-pentane gave 2.6 grams of 3-(3',5'-dimethoxyphenacylidene)phthalimidine, m.p. 150° C. Analysis shows 69.87% carbon, 4.91% hydrogen and 4.55% nitrogen as against calculated values of 69.89%, 4.89% and 4.53% for $C_{18}H_{15}NO_4$.

Within the generic class of compounds disclosed by formulas (I) and (II), and illustrated by the preceding examples, a preferred group consists of those compounds wherein a and b are 0, R is phenyl or substituted phenyl, R' is hydrogen an Z is OH.

EXAMPLE 30

The post-emergence herbicidal activity of various compounds of this invention is demonstrated as follows. The active ingredients are applied in spray form to 14–21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at various rates (kg per hectare) of active ingredient. The treated plants are placed in a greenhouse and the effects are observed and recorded after approximately 2 weeks.

There are eleven different plant species in each test pan. Six os these species are broadleaf plants including Canada thistle, cocklebur, velvetleaf, morningglory, lambsquarters and smartweed. The remaining five species are narrow-leaf plants and include nutsedge, quackgrass, johnsongrass, downy brome and barnyardgrass. The observations are made in terms of percent injury to each treated plant species. The results with compounds of this invention are reported below, and it should be understood that where a figure is not given for any individual plant species, the percent injury observed was less than 25% at the rate noted.

Employing the compound of Example 1, injury of 25–49% is observed on Canada thistle and cocklebur at 56 kg/hectare. Employing the compound of Example 2, injury of 25–49% is observed on cocklebur and barnyardgrass at 56 kg/hectare. Employing the compound of Example 3, injury of 25–49% is observed on cocklebur at 56 kg/hectare. Employing the compound of Example 4, injury of 25–49% is observed on cocklebur and lambsquarters at 56 kg/hectare. Employing the compound of Example 6, injury of 25–49% is observed on morningglory and smartweed and 50–74% injury on cocklebur at 56 kg/hectare. Employing the compound of Example 8, injury of 25–49% is observed on Canada thistle and morningglory at 28 kg/hectare. Employing the compound of Example 9, injury of 25–49% is observed on cocklebur, velvetleaf and quackgrass at 28 kg/hectare. Employing the compound of Example 10, injury of 25–49% is observed on Canada thistle, cocklebur and morningglory and 50–74% injury on velvetleaf at 56 kg/hectare. Employing the compound of Example 11, injury of 25–49% is observed on cocklebur and morningglory at 56 kg/hectare. Employing the compound of Example 12, injury of 25–49% is observed on cocklebur, velvetleaf and morningglory at 56 kg/hectare. Employing the compound of Example 13, injury of 25–49% is observed on cocklebur at 56 kg/hectare. Employing the compound of Example 14, injury of 25–49% is observed on cocklebur and morningglory at 56 kg/hectare. Employing the compound of Example 16, injury of 25–49% is observed on velvetleaf at 56 kg/hectare. Employing the compound of Example 17, injury of 25–49% is observed on cocklebur and 50–74% injury on morningglory at 56 kg/hectare. Employing the compound of Example 19, injury of 25–49% is observed on cocklebur, velvetleaf, morningglory, lambsquarters and smartweed at 28 kg/hectare. Employing the compound of Example 20, injury of 25–49% is observed on morningglory and lambsquarters at 28 kg/hectare. Employing the compound of Example 24, injury of 25–49% is observed on velvetleaf, morningglory, lambsquarters and barnyardgrass and 50–74% injury on cocklebur at 56 kg/hectare. Employing the compound of Example 25, injury of 25–49% is observed on cocklebur at 56 kg/hectare. Employing the compound of Example 26, injury of 25–49% is observed on cocklebur at 56 kg/hectare. Employing the compound of Example 27, injury of 25–49% is observed on Canada thistle, cocklebur, velvetleaf, morningglory and smartweed at 56 kg/hectare. Employing the compound of Example 29, injury of 25–49% is observed on Canada thistle at 11.2 kg/hectare.

Employing the compound of Example 18 at 56 kg/hectare, none of the plant species were observed to have injury of 25% or more. The same was true of the compounds of Examples 5, 7 and 28 at 28 kg/hectare, and the compound of Examples 10, 15 and 21–23 at 11.2 kg/hectare.

EXAMPLE 31

The pre-emergent herbicidal activity of various compounds of this invention is demonstrated as follows. A good grade of top soil is placed in aluminum pans and compacted to a depth of ⅛ to ¼ inch from the top of each pan. A predetermined number of seeds or vegetable propagules of each of several plant species are placed on top of the soil in each pan and then pressed down. Herbicidal compositions (as described in Example 8) employing the active ingredients of this invention are applied by admixture with or incorporation in the top layer of soil.

In this method, the soil required to cover the seeds and propagules is weighed and admixed with a herbicidal composition containing a known amount of active ingredient. The pans are then filled with the admixture and leveled. Watering is carried out by permitting the soil in the pans to absorb moisture through apertures in the pan bottoms. The seed and propagule containing pans are placed on a wet sand bench and maintained for approximately 2 weeks under ordinary conditions of sunlight and watering. At the end of this period the number of emerged plants of each species is noted and compared to an untreated control. In the tests for pre-emergent activity, the same 11 plant species enumerated in Example 30 are used. Here again, no figure is given if the percent control of an individual species is less than 25%.

Employing the compound of Example 1, control of 50–74% is observed on lambsquarters at 56 kg/hectare. Employing the compound of Example 2, control of 25–49% is observed on morningglory and control of 50–74% on lambsquarters and control of 75–100% on nutsedge at 56 kg/hectare. Employing the compound of Example 3, control of 25–49% is observed on cocklebur and control of 75–100% on lambsquarters at 56 kg/hectare. Employing the compound of Example 6, control of 50–74% is observed on lambsquarters at 56 kg/hectare. Employing the compound of Example 17, control of 75–100% is observed on lambsquarters at 56 kg/hectare. Employing the compound of Example 19, control of 25–49% is observed on downy brome and control of 50–74% on velvetleaf and control of 75–100% on lambsquarters and smartweed at 11.2 kg/hectare. Employing the compound of Example 21, control of 25–49% is observed on Canada thistle and morningglory and control of 75–100% on lambsquarters at 11.2 kg/hectare. Employing the compound of Example 24, control of 75–100% is observed on nutsedge at 56 kg/hectare.

Employing the compounds of Examples 4, 10–13, 18 and 23 at 56 kg/hectare, none of the plant species were observed to have been controlled to 25% or more. The same was true of the compound of Example 9 at 28 kg/hectare, and the compounds of Examples 5, 7, 8, 14–16, 20, 22, 25 and 28 at 11.2 kg/hectare.

From the tests results presented in Examples 30 and 31, it can be seen that the herbicidal activity of the compounds of this invention is selective in nature. Only certain particular plant species are found to be injured or controlled by each specific compound. In this regard it should be recognized that each individual plant species selected for the above tests is a representative member of a recognized family of plants.

As regards the reduction of injury to crop plants which are contacted with other herbicides, tests were conducted with a number of compounds of the present invention in conjunction with several commercially available, pre-emergent herbicides. The crops employed in these tests were rice, sorghum and wheat, while the herbicides, identified here by their common names, were butachlor, alachlor and triallate. The test procedures are as described below.

A good grade of top soil is placed in a container and compacted to a depth of about 1.27 cm from the top of the container. A pre-determined number of seeds of each of the crops to be tested are placed on top of the soil in the container. A quantity of soil necessary to fill the container is measured out and placed in a second container. A measured amount of a compound of this invention, dispersed or dissolved in a suitable carrier, is applied to the surface of the soil in the second container, and a measured amount of one of the pre-emergent herbicides above, dispersed or dissolved in a suitable carrier, is then also applied to the soil in the second container.

The soil thus treated is thoroughly mixed to provide a substantially uniform distribution of the compound of the invention and the pre-emergent herbicide. The seeds in the first container are then covered with the treated soil. The container is placed on a sand bench in a greenhouse and watered from below as needed. The plants which grow are observed after about 21 days, and the number of plants of each crop is noted. This is then compared with the plants in another container in which the soil was treated only with the pre-emergent herbicide, and a further container in which there was no soil treatment at all. Since various individual compounds of this invention were tested at different times during the year, corresponding tests were made at those times with the herbicide alone and with the untreated soil. This should serve to minimize or eliminate any differences in relative readings due to seasonal differences in sunlight, day length and temperature.

Comparison of the untreated crop plants with the herbicide treatment alone determines the percent of plant inhibition caused by the herbicide treated. A similar comparison of the untreated crop plants with those having the herbicide/compound of the invention treatment then determines the percent of plant inhibition of this combined treatment. Where the second percentage is below the first percentage by at least 8–10%, it is considered that the added compound of the present invention has exerted a safening action by meaningfully reducing the crop injury caused by the herbicide alone.

In the following table, herbicide A is triallate, herbicide B is alachlor and herbicide C is butachlor. Where an asterisk appears, the difference between the observed percentages did not reach the minimum range noted above. Indeed, it was noted that in some instances the addition of a compound of this invention to the treatment caused increased inhibition of the crop plants rather than safening action.

TABLE

| Herbi-cide | Rate (kg/h) | Compound of Example | Rate (kg/h) | Reduction in percent inhibition | | |
|---|---|---|---|---|---|---|
| | | | | Rice | Sorghum | Wheat |
| A | .56 | 2 | 8.96 | * | * | * |
| B | 2.24 | 2 | 8.96 | * | * | * |
| C | 4.48 | 2 | 8.96 | * | * | * |
| A | .56 | 4 | 8.96 | 17 | * | 30 |
| B | 4.48 | 4 | 8.96 | * | * | 35 |
| C | 4.48 | 4 | 8.96 | * | 10 | * |
| A | .56 | 5 | 4.48 | * | * | * |
| B | 2.24 | 5 | 4.48 | * | * | 10 |
| C | 4.48 | 5 | 4.48 | * | * | 13 |
| A | .56 | 7 | 8.96 | 8 | * | 30 |
| B | 2.24 | 7 | 8.96 | 15 | * | 23 |
| C | 4.48 | 7 | 8.96 | 18 | * | * |
| A | .56 | 8 | 8.96 | * | * | 10 |
| B | 4.48 | 8 | 8.96 | * | * | 8 |
| C | 4.48 | 8 | 8.96 | 28 | * | 13 |
| A | .56 | 9 | 8.96 | 8 | 8 | * |
| B | 2.24 | 9 | 8.96 | * | * | * |
| C | 4.48 | 9 | 8.96 | * | 15 | * |
| A | .56 | 11 | 8.96 | 12 | * | * |
| B | 4.48 | 11 | 8.96 | * | * | * |
| C | 4.48 | 11 | 8.96 | * | 33 | 13 |
| A | .56 | 12 | 8.96 | * | * | 55 |
| B | 2.24 | 12 | 8.96 | * | * | * |
| C | 4.48 | 12 | 8.96 | * | 15 | * |
| A | .56 | 13 | 4.48 | * | * | * |
| B | 4.48 | 13 | 4.48 | * | * | * |
| C | 4.48 | 13 | 4.48 | * | * | 18 |
| A | .56 | 14 | 8.96 | 10 | * | * |
| B | 4.48 | 14 | 8.96 | * | * | * |
| C | 4.48 | 14 | 8.96 | * | * | * |
| A | .56 | 15 | 8.96 | * | * | * |
| B | 4.48 | 15 | 8.96 | * | * | * |
| C | 4.48 | 15 | 8.96 | 25 | * | 33 |
| A | .56 | 16 | 4.48 | * | * | 20 |
| B | 4.48 | 16 | 4.48 | * | * | * |
| C | 4.48 | 16 | 4.48 | 15 | 9 | 23 |
| A | .56 | 17 | 8.96 | * | * | * |
| B | 4.48 | 17 | 8.96 | * | * | 25 |
| C | 4.48 | 17 | 8.96 | 20 | * | 13 |
| A | .56 | 18 | 8.96 | 14 | * | * |
| B | 2.24 | 18 | 8.96 | * | * | * |
| C | 4.48 | 18 | 8.96 | * | * | * |
| A | .56 | 20 | 8.96 | * | 53 | * |
| B | 4.48 | 20 | 8.96 | * | * | * |
| C | 4.48 | 20 | 8.96 | 20 | 8 | 35 |
| A | .56 | 22 | 8.96 | * | * | 8 |
| B | 4.48 | 22 | 8.96 | * | * | * |
| C | 4.48 | 22 | 8.96 | * | * | * |
| A | .42 | 23 | 4.48 | 10 | * | * |
| B | 2.24 | 23 | 4.48 | * | * | * |
| C | 4.48 | 23 | 4.48 | 8 | * | 8 |
| A | .56 | 24 | 8.96 | 15 | * | * |
| B | 4.48 | 24 | 8.96 | * | * | * |
| C | 4.48 | 24 | 8.96 | 10 | * | 15 |
| A | .42 | 25 | 4.48 | 10 | * | 13 |
| B | 2.24 | 25 | 4.48 | 23 | * | * |
| C | 4.48 | 25 | 4.48 | * | * | 23 |
| A | .56 | 28 | 8.96 | 8 | * | * |
| B | 4.48 | 28 | 8.96 | * | * | 8 |
| C | 4.48 | 28 | 8.96 | * | * | * |

The compositions of compounds of this invention, including concentrations which require dilution prior to application to the plants, contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required, from about 0.1 to 2.0 parts by weight of the inert liquid extender can be replaced by a corrosion inhibitor or antifoaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic, non-ionic and amphoteric agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredients of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, pesticides or the like, it is preferred to employ the compositions of this invention alone with sequential treatments with the other phytotoxicants, fertilizers or the like for maximum effect. For example, a field could be sprayed with a composition of this invention either before or after being treated with fertilizers, other phytotoxicants or the like. The compositions of this invention can also be admixed with the other materials, e.g., fertilizers, other phytotoxicants, etc., and applied in a single treatment.

When operating in accordance with the present invention, effective amounts of the phthalimidines are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray. The application of compositions to aquatic plants is usually carried out by adding the compositions to the aquatic media in the area where control of the aquatic plants is desired.

The application of an effective amount of the compounds of this invention to the plant is essential and critical for the practice of the present invention. The exact amount of active ingredient to be employed is dependent upon such factors as the particular plant species and stage of development thereof, as well as the specific compound employed and the type of response desired. In foliar and soil treatments for the control of vegetative growth, the active ingredients are applied in amounts from about 11.2 to about 56 or more kilograms per hectare. In treatments of soil to provide a crop safening action, application rates of 8.96 kg/hectare or less can be employed. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound having a formula selected from

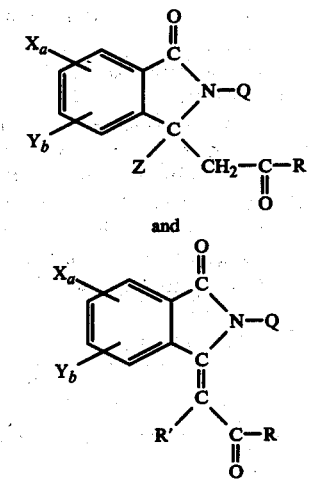

wherein R is phenyl, naphthyl, biphenylyl or substituted phenyl, there being from 1 to 5 substituents selected from alkyl of 1 to 3 carbon atoms, alkoxy of 1 to 4 carbon atoms, halogen, nitro and trifluoromethyl, R' is hydrogen or bromine, X is halogen, Y is hydroxy, alkoxy of 1 to 4 carbon atoms, nitro or amino, a is 0 to 4, b is 0 to 2, the sum of a + b is 0 to 4, Q is hydrogen, alkyl of 1 to 3 carbon atoms, phenyl, halophenyl, nitrophenyl, trifluoromethylphenyl, tolyl, anisyl or tosylamino, and Z is hydrogen or OH.

2. A compound as defined in claim 1 wherein said formula is

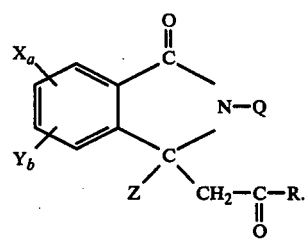

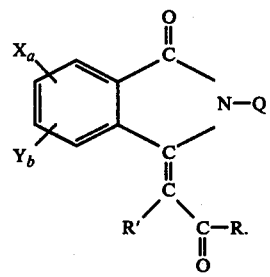

3. A compound as defined in claim 2 wherein a and b are 0.

4. A compound as defined in claim 3 wherein Z is OH.

5. A compound as defined in claim 3 wherein Q is hydrogen.

6. A compound as defined in claim 3 wherein R is said substituted phenyl.

7. A compound as defined in claim 3 wherein R is phenyl.

8. A compound as defined in claim 3 wherein Z is OH and Q is hydrogen.

9. A compound as defined in claim 8 wherein R is said substituted phenyl.

10. A compound as defined in claim 8 wherein R is phenyl.

11. A compound as defined in claim 1 wherein said formula is

12. A compound as defined in claim 11 wherein a and b are 0.

13. A compound as defined in claim 12 wherein R' is hydrogen.

14. A compound as defined in claim 12 wherein Q is hydrogen.

15. A compound as defined in claim 12 wherein R is phenyl.

16. A compound as defined in claim 12 wherein R is said substituted phenyl.

17. A compound as defined in claim 12 wherein R' and Q are hydrogen.

18. A compound as defined in claim 17 wherein R is phenyl.

19. A compound as defined in claim 17 wherein R is said substituted phenyl.

20. A compound as defined in claim 1 wherein a and b are zero, R is phenyl or said substituted phenyl, R' is hydrogen and Z is OH.

* * * * *